United States Patent
Iversen et al.

(10) Patent No.: US 10,765,630 B2
(45) Date of Patent: Sep. 8, 2020

(54) METHODS AND COMPOSITIONS TO TREAT ENTEROPATHIC ARTHRITIS

(71) Applicant: SEN-JAM PHARMACEUTICAL LLC, Huntington, NY (US)

(72) Inventors: Jacqueline Iversen, Lloyd Harbor, NY (US); Thomas A. Dahl, Guilford, CT (US)

(73) Assignee: SEN-JAM PHARMACEUTICAL LLC, Huntington, NY (US)

( * ) Notice: Subject to any disclaimer, the term of this patent is extended or adjusted under 35 U.S.C. 154(b) by 0 days.

(21) Appl. No.: 16/355,147

(22) Filed: Mar. 15, 2019

(65) Prior Publication Data
US 2019/0282499 A1 Sep. 19, 2019

Related U.S. Application Data

(60) Provisional application No. 62/643,952, filed on Mar. 16, 2018.

(51) Int. Cl.
| | | |
|---|---|---|
| *A61K 9/68* | (2006.01) | |
| *A61K 31/192* | (2006.01) | |
| *A61K 31/4465* | (2006.01) | |
| *A61K 31/4545* | (2006.01) | |
| *A61K 31/616* | (2006.01) | |
| *A61K 31/4535* | (2006.01) | |
| *A61K 9/00* | (2006.01) | |
| *A61P 19/02* | (2006.01) | |
| *A61P 19/00* | (2006.01) | |
| *A61P 1/00* | (2006.01) | |

(52) U.S. Cl.
CPC .......... *A61K 9/0058* (2013.01); *A61K 9/0056* (2013.01); *A61K 31/192* (2013.01); *A61K 31/4465* (2013.01); *A61K 31/4535* (2013.01); *A61K 31/4545* (2013.01); *A61K 31/616* (2013.01); *A61P 1/00* (2018.01); *A61P 19/00* (2018.01); *A61P 19/02* (2018.01)

(58) Field of Classification Search
CPC ............... A61K 31/192; A61K 31/445; A61K 31/4535; A61K 31/4545; A61K 31/616; A61K 31/4465; A61K 45/06; A61K 9/0056; A61K 9/0058; A61P 1/00; A61P 19/00; A61P 19/02; A61P 19/08
See application file for complete search history.

(56) References Cited

U.S. PATENT DOCUMENTS

| 8,067,451 | B2 | 11/2011 | Tidmarsh et al. |
| 9,198,999 | B2 | 12/2015 | Plachetka |
| 9,415,036 | B2 * | 8/2016 | Bastianelli ............ A61K 35/32 |
| 9,629,847 | B2 | 4/2017 | Leighton |
| 9,669,093 | B2 | 6/2017 | Medich et al. |
| 9,783,602 | B2 | 10/2017 | Dutzar et al. |
| 2004/0224876 | A1 | 11/2004 | Jost-Price et al. |
| 2005/0192261 | A1 * | 9/2005 | Jost-Price ............ A61K 31/00 514/171 |
| 2009/0110679 | A1 | 4/2009 | Li et al. |
| 2013/0108697 | A1 * | 5/2013 | Gundo ................. A61K 9/2072 424/468 |
| 2018/0042877 | A1 | 2/2018 | Bannister et al. |
| 2019/0060297 | A1 * | 2/2019 | Iversen ................... A61P 29/00 |

FOREIGN PATENT DOCUMENTS

WO 2016154028 A1 9/2016

OTHER PUBLICATIONS

Holden et al., "Enteropathic arthritis", 2003, Rheum. Dis. Clin. N. Am., 29(3), pp. 513-530. (doi:10.1016/S0889-857X(03)00043-7) (Year: 2003).*
Peluso, R. et al., "Enteropathic Spondyloarthritis: From Diagnosis to Treatment," Clinical and Developmental Immunology, vol. 2013, Article ID 631408, pp. 1-12; [online], [retrieved on Dec. 23, 2013], Retrieved from the Internet <URL: http://downloads.hindawi.com/journals/cdi/2013/631408.pdf>.
Pullar, T. et al., "A rheumatological dilemma: is it possible to modify the course of rheumatoid arthritis? Can we answer the question?" Annals of the Rheumatic Diseases, vol. 44, 1985, pp. 134-140.
Caroselli, C. et al. "Ulcerative Colitis Masked by Giant Urticaria," International Journal of Immunopathology and Pharmacology, vol. 20, No. 1, 2007, pp. 181-184.
PCT/US2019/022544 International Search Report and Written Opinion dated May 17, 2019.
Teh, L.G. et al., "Does the addition of ketotifen to non-steroidal anti-inflammatory drugs confer any additional benefit in rheumatoid arthritis?" Br. J. clin. Pharmac. (1984), 17, pp. 157-159.
Klein, Amir et al., "Non Steroidal Anti-Inflammatory Drugs and Inflammatory Bowel Disease," Pharmaceuticals 2010, 3, 1084-1092; doi:10.3390/ph3041084.
Mican, JoAnn M. et al., "Arthritis and mast cell activation," J Allergy Clin Immunol, 1990; pp. 677-683.
Arthritis Foundation, "What is Ankylosing Spondylitis?" [online], [retrieved on Dec. 21, 2017], Retrieved from the Internet <URL: http://www.arthritis.org/about-arthritis/types/ankylosing-spondylitis . . . >.

* cited by examiner (Continued)

*Primary Examiner* — My-Chau T. Tran
(74) *Attorney, Agent, or Firm* — Hoffmann & Baron, LLP

(57) ABSTRACT

The present invention is a method of treating enteropathic arthritis in a human subject in need thereof. The method comprises administering an effective amount of a pharmaceutical composition to the subject, wherein the pharmaceutical composition comprises: a) a non-steroidal anti-inflammatory drug (NSAID), and/or a salt thereof; and b) a co-agent selected from the group consisting of: fexofenadine, ketotifen, desloratadine, cetirizine, salts thereof and combinations thereof.

16 Claims, No Drawings

METHODS AND COMPOSITIONS TO TREAT ENTEROPATHIC ARTHRITIS

This application claims the benefit of U.S. Provisional Application Ser. No. 62/643,952, filed Mar. 16, 2018, which is incorporated herein by reference in its entirety.

FIELD OF THE INVENTION

The present invention relates to methods, and compositions, for treating enteropathic arthritis.

BACKGROUND OF THE INVENTION

Enteropathic arthritis (also known as enteroarthritis) is a spondyloarthritis which occurs in patients with gastrointestinal diseases, such as, inflammatory bowel diseases (IBDs) and other diseases, such as, for example, Whipple's disease, celiac disease, and disorders resulting from intestinal bypass surgery (e.g., jejunoileal bypass). (Orlando et al., "Gastrointestinal lesions associated with spondyloarthropathies," *World Journal of Gastroenterology,* 15(20):2443-2448 (2009).)

Spondyloarthritis is typically classified into two subsets: axial spondyloarthritis and peripheral spondyloarthritis. Subcategories of axial spondyloarthritis are i. ankylosing spondylitis (also known as radiographic axial spondyloarthritis) and ii. non-radiographic axial spondyloarthritis. Axial spondyloarthritis is characterized by long-term inflammation of the joints of the spine, sometimes also including the joints where the spine joins the pelvis. Peripheral spondyloarthritis is characterized by inflammation of the joints in the arms and legs, most often the lower legs.

Attacks or flares of the joint inflammation are typical in both forms of spondyloarthritis. These flares usually have a rapid onset, typically setting in within 48 hours. The flares sometimes disappear within about six months, but inflammation can become chronic in some people. The symptoms of gastrointestinal diseases sometimes flare along with the symptoms of spondyloarthritis in enteropathic arthritis.

Inflammatory bowel diseases involve chronic inflammation of the digestive tract. The most common forms of IBD are ulcerative colitis (UC) and Crohn's disease (CD). Ulcerative colitis is characterized by inflammation and sores in the inner lining of the large intestine (colon) and rectum. Crohn's disease is characterized by inflammation anywhere in the digestive tract (including both the small and large intestines) and can spread deeper into the tissues. Less severe forms of IBDs include collagenous colitis and lymphocytic colitis. Symptoms of IBD include abdominal pain, diarrhea, weight loss, hematochezia, tenesmus, fever and nutritional deficiencies Inflammatory bowel diseases can be devastating and can lead to life-threatening complications.

Currently, it is beneficial if the management of patients with enteropathic arthritis involves an active cooperation between gastroenterologist and rheumatologist.

Treatment of enteropathic arthritis includes the use of disease-modifying anti-rheumatic drugs (DMARDs), anti-TNFα agents, and immunosuppressants (e.g., corticosteroids, methotrexate, azathioprine, cyclosporine, and leflunomide). However, these pharmaceuticals have varying degrees of efficacy in one of both components of enteropathic arthritis. For example, some anti-TNFα agents, especially infliximab and adalimumab, have been successful in treating both the intestinal inflammation and the joint pain in patients with enteropathic arthritis, especially in patients with the CD component; however, etanercept is effective only to control joint symptoms, i.e., not gastrointestinal symptoms. Further, most of the current pharmaceutical treatments tend to have significant adverse effects.

Additionally, sulfasalazine and 5-aminosalicylic acid are often used for the treatment of UC, and their effectiveness has also been shown for the management of mild peripheral arthritis. However, their effectiveness on CD is still questionable. Further, these drugs have no effect on the progression of joint damage and their usefulness in the axial subset is marginal; and they do not seem to prevent the onset of gastrointestinal inflammation.

It has been reported that patients may respond to anti-inflammatory drugs, useful to control joint inflammation. However, such drugs may exacerbate IBD (Kaufmann et al., "NSAIDs activate quiescent inflammatory bowel disease," *Annals of Internal Medicine.* 107(4):513-516 (1987); Bjarnason et al., "Side effects of NSAIDs on the small and large intestine in humans," *Gastroenterology.* 104(6):1832-1847 (1993)). For example, nonsteroidal anti-inflammatory drugs (NSAIDs) have been found to cause the appearance of small intestine and colon ulcers (Kaufman et al., "Colonic ulceration associated with NSAIDs: report of three cases," *Diseases of the Colon and Rectum.* 39(6):705-710 (1996)). As a consequence, in order to manage joint symptoms, NSAIDs may be recommended only for patients who experience mild exacerbations of gastrointestinal distress; and even then, NSAID use should be limited to the lowest effective dose and only for short periods of time.

In fact, the main factor limiting NSAID use in any ailment is the concern for the development of gastrointestinal toxicity including mucosal injury in the form of erosions and ulcers; upper gastrointestinal (GI), small bowel or colonic bleeding; and sometimes perforation and obstruction due to stricture formation (Wolfe et al., "Gastrointestinal toxicity of NSAIDs." *N. Engl. J. Med.* 340:1888-1899 (1999)). NSAIDs may also cause a nonspecific type of colitis and small intestinal inflammation with associated complications of chronic blood or protein loss (Bjarnason et al., *Gastroenterology.* 104:1832-1847 (1993)). Endoscopic features of NSAID-induced colonic damage include sharply demarcated or circumferential ulcers which are usually reversible upon discontinuation of the drug (Kurahara et al., "Clinical and endoscopic features of NSAID-induced colonic ulcerations." *Am. J. Gastroenterol.* 96:473-480 (2001)). It is estimated that NSAID use by patients with arthritis in the United States causes over 100,000 hospitalizations annually for GI complications, one fifth of which are estimated to be due to lower GI complications (Laine et al., "Systematic review: the lower gastrointestinal adverse effects of NSAIDs." *Aliment Pharmacol. Ther.* 24:751-767 (2006)). A review of the literature of lower GI adverse effects of NSAIDs revealed that there was a statistically significant increase in adverse outcome rates associated with the use of NSAIDs in patients with lower GI bleeding, perforation and complicated diverticular disease (Guslandi M. "Exacerbation of inflammatory bowel disease by NSAIDs and cyclooxygenase-2 inhibitors: fact or fiction?" *World J. Gastroenterol.*12:1509-1510 (2006)).

Further, it has been found that NSAID use may initiate IBD, or cause reactivation of quiescent disease and induce GI complications (Fries et al., "Toward an epidemiology of gastropathy associated with NSAID use." *Gastroenterology.* 96(Suppl.):647-655 (1996)). Several studies have implicated NSAID use in the onset or exacerbation of IBD (Singh et al., "Do NSAIDs, antibiotics, infections, or stress trigger flares in IBD?" *Am. J. Gastroenterol.* 104:1298-1313 (2009); Felder et al., "Effects of NSAIDs on IBD: a case-control study." *Am. J. Gastroenterol.* 95:1949-1954 (2000)). Using clinical evaluation and fecal calprotectin measurements, it was demonstrated that non-selective NSAIDs were associated with a 17-28% relapse rate within nine days of ingestion of the drug, in patients with IBD (Takeuchi et al., "Prevalence and mechanism of NSAID-induced clinical relapse in patients with inflammatory bowel disease." *Clin. Gastroenterol Hepatol.* 4:196-202 (2006)). Also, retrospectively reviewed files of outpatients with IBD showed that treatment with NSAIDs was associated with disease relapse (Meyer et al., "Relapse of IBD associated with use of NSAIDs." *Dig. Dis. Sci.* 51:168-172 (2006)). Thus, plainly, the use of NSAIDs in patients with diseases that have a gastrointestinal component, such as enteropathic arthritis, is generally contraindicated.

Clearly, there is a need for a more effective and accessible manner by which to treat individuals with enteropathic arthritis.

SUMMARY OF THE INVENTION

In one embodiment, the present invention is a method of treating enteropathic arthritis in a human subject in need thereof. The method comprises administering an effective amount of a pharmaceutical composition to the subject. The pharmaceutical composition comprises a) a non-steroidal anti-inflammatory drug (NSAID); and b) a co-agent selected from the group consisting of: fexofenadine, ketotifen, desloratadine, cetirizine, salts thereof and combinations thereof.

Examples of NSAIDs include aspirin, ibuprofen, naproxen, diclofenac, diflunisal, etodolac, indomethacin, ketoprofen, ketorolac, meloxicam, nabumetone, oxaprozin, piroxicam, salsalate, sulindac, and/or tolmetin.

In one embodiment, the NSAID is naproxen sodium and the co-agent is fexofenadine. In one embodiment, the amount of naproxen sodium is about 220 mg to about 880 mg, and the amount of fexofenadine is about 60 mg to about 180 mg. In one embodiment, the naproxen sodium and the fexofenadine are combined in one unit dose. In one embodiment, the ibuprofen and the fexofenadine is in the form of a tablet, lozenge or chewing gum.

In one embodiment, the present invention is a pharmaceutical composition comprising a) an NSAID, and/or a salt thereof; and b) a co-agent selected from fexofenadine, ketotifen, desloratadine, cetirizine salts thereof and combinations thereof. In one embodiment, the pharmaceutical composition is naproxen sodium in an amount of about 220 mg to about 880 mg, and fexofenadine in an amount of about 25 mg to about 200 mg.

DETAILED DESCRIPTION OF THE INVENTION

In one embodiment, the present invention is directed to methods, and pharmaceutical compositions, to treat enteropathic arthritis in human subjects in need thereof. The methods include the administration of particular pharmaceutical compositions.

Throughout this specification, quantities are defined by ranges, and by lower and upper boundaries of ranges. Each lower boundary can be combined with each upper boundary to define a range. The lower and upper boundaries should each be taken as a separate element.

The methods of the present invention comprise the administration of a pharmaceutical composition to a human subject, in need thereof, in an amount which is effective to treat enteropathic arthritis. A human subject in need thereof is a human who suffers from the symptoms of, and/or has been diagnosed as having, enteropathic arthritis. Administration includes administration by a physician or self-administration.

The pharmaceutical composition comprises a) at least one non-steroidal anti-inflammatory drug ("NSAID") and/or salts thereof, and b) a co-agent and/or salts thereof.

The NSAID of the present invention includes any NSAID and salts thereof. Examples of suitable NSAIDs include, but are not limited to, aspirin (i.e., acetylsalicylic acid); ibuprofen (i.e., isobutylphenylpropanoic acid); naproxen (i.e., 6-methoxy-α-methyl-2-naphthaleneacetic acid); diclofenac (i.e., 2-[(2,6-dichlorophenyl)-amino]benzene acetic acid); diflunisal (i.e., 2',4'-difluoro-4-hydroxybiphenyl-3-carboxylic acid); etodolac (i.e., (RS)-2-(1,8-diethyl-4,9-dihydro-3H-pyrano[3,4-b]indol-1-yl)acetic acid); indomethacin (i.e., 2-{1-[(4-chlorophenyl)-carbonyl]-5-methoxy-2-methyl-1H-indol-3-yl}acetic acid); ketoprofen (i.e., 3-benzoyl-α-methyl-benzeneacetic acid); ketorolac (i.e., 2-amino-2-(hydroxymethyl)-1,3-propanediol); meloxicam (i.e., 4-hydroxy-2-methyl-N-(5-methyl-2-thiazolyl)-2H-1,2-benzothiazine-3-carboxamide-1,1-dioxide); nabumetone (i.e., 4-(6-methoxy-2-naphthyl)-2-butanone); oxaprozin (i.e., 3-(4,5-diphenyl-1,3-oxazol-2-yl)propanoic acid); piroxicam (i.e., 4-hydroxy-2-methyl-N-2-pyridinyl-2H-1,2-benzothiazine-3-carboxamide 1,1-dioxide); salsalate (i.e., 2-(2-hydroxybenzoyl)-oxybenzoic acid); sulindac (i.e., {(1Z)-5-fluoro-2-methyl-1-[4-(methylsulfinyl)-benzylidene]-1H-indene-3-yl}acetic acid); and tolmetin (i.e., [1-methyl-5-(4-methylbenzoyl)-1H-pyrrol-2-yl]acetic acid).

Suitable co-agents include desloratadine (i.e., 8-chloro-6, 11-dihydro-11-(4-piperdinylidene)-5H-benzo[5,6]cyclohepta[1,2-b]pyridine); fexofenadine (i.e., (±)-4-[1 hydroxy-4-[4-(hydroxydiphenylmethyl)-1-piperidinyl]-butyl]-α, α-dimethyl benzeneacetic acid); ketotifen; cetirizine; and salts of such co-agents.

The NSAIDs and co-agents include all pharmaceutically acceptable versions of the NSAIDs and co-agents, including, for example, stereoisomers and/or any mixtures thereof, all pharmaceutically acceptable zwitterions and/or any mixtures thereof, all pharmaceutically acceptable polymorphic forms and/or any mixtures thereof, and all pharmaceutically acceptable complexes (including solvates) and/or any mixtures thereof.

Salts include all salts of NSAIDs and all salts of co-agents which are pharmaceutically acceptable (i.e., non-toxic at therapeutically effective doses). And, salts include their racemates, enantiomers, or any mixtures thereof.

Particularly suitable salts of the NSAIDs comprise alkali-metal salts (e.g., sodium and/or potassium salts), alkaline earth metal salts (e.g., magnesium and/or calcium salts), aluminum salts, ammonium salts, salts of suitable organic bases (e.g., salts of alkylamines and/or -methyl-D-glutamine), salts of amino acids (e.g., salts of arginine and/or lysine). The NSAID salts also include all enantiomeric salts formed with pharmaceutically acceptable chiral acids and/or bases and/or any mixtures of enantiomers of such salts (e.g., (+) tartrates, (−) tartrates and/or any mixtures thereof including racemic mixtures). For example, a typical salt of an NSAID is naproxen sodium.

Examples of suitable salts of the co-agents include ketotifen fumarate, fexofenadine hydrochloride and cetirizine hydrochloride.

Enteropathic arthritis is a disease which has an arthritic component and a gastrointestinal component.

The arthritic component is a spondyloarthritis, which can be axial spondyloarthritis and/or peripheral spondyloarthritis. Axial spondyloarthritis can be i. ankylosing spondylitis and/or ii. non-radiographic axial spondyloarthritis. Examples of typical symptoms of spondyloarthritis include inflammation and pain of the joints of the spine, pelvic joints, and the joints of the arms and legs.

The gastrointestinal component includes gastrointestinal disorders/diseases, such as, inflammatory bowel diseases (IBDs) and other diseases, such as, for example, Whipple's disease, celiac disease, and disorders resulting from jejunoileal bypass surgery. Inflammatory bowel diseases include, for example, collagenous colitis, lymphocytic colitis, ulcerative colitis and Crohn's Disease.

The symptoms of gastrointestinal disorders vary dependent upon which particular disorder/disease is present. For example, symptoms of ulcerative colitis include inflammation and sores in the inner lining of the large intestine and rectum; symptoms of Crohn's Disease include inflammation anywhere in the digestive tract and deeper tissues. Symptoms which are common to IBDs and other gastrointestinal diseases/disorders include abdominal pain, cramping especially after meals, diarrhea, weight loss, hematochezia, tenesmus, fever, nutritional deficiencies, vomiting, constipation, fatigue, and anemia.

In the present specification, the term "treat" includes "reduce" and/or "prevent" and/or "shorten duration of an episode" of any symptom of either, or both, the arthritic component and/or gastrointestinal component of enteropathic arthritis. Treatment also includes inhibiting the progression of either component (or both components) of enteropathic arthritis. For example, the progression of joint damage and/or intestinal ulcerations is inhibited.

In one embodiment, treatment continues for an extended period with a regular schedule of administration (e.g., daily administration, or substantially daily administration) of a pharmaceutical composition of the present invention for weeks, or months, or years. In another embodiment, a pharmaceutical composition of the present invention is administered for episodic pain related to enteropathic arthritis. That is, a subject is administered a pharmaceutical composition on an as-needed basis.

Typically, symptoms are reduced by at least about 10%, at least about 20%, at least about 30%, at least about 40%, at least about 50%, at least about 60%, at least about 70%, at least about 80%, at least about 90%, or at least about 100%. Symptoms of one or both components of enteropathic arthritis (i.e., the spondyloarthritis component and gastrointestinal component) is/are reduced.

In another embodiment, the pharmaceutical compositions of the present invention are administered to enteropathic arthritis patients (e.g., subjects who are suffering from, or diagnosed with, enteropathic arthritis) to treat any episodic pain which is unrelated to their underlying enteropathic arthritis. Examples of such episodic pain unrelated to the enteropathic arthritis include: pain from headache, backache, fever, toothache, menstrual cramps, and/or cold/flu, sore muscles, sprained limbs, etc. Before the present invention, NSAID pain relievers were contradicted for patients with enteropathic arthritis due to the gastrointestinal distress associated with NSAIDs.

It has unexpectedly been found that the components of the compositions of the present invention have a synergistic effect when treating enteropathic arthritis in human subjects, and when treating unrelated episodic pain in patients who suffer from enteropathic arthritis. For example, taking an NSAID (especially on a daily basis) is associated with adverse gastrointestinal effects (e.g., upset stomach, ulcers). Moreover, regular administration of an NSAID to subjects who have gastrointestinal disorders/diseases is typically strongly contraindicated. However, when the NSAIDs of the present invention are taken in combination with the co-agents, they have surprisingly been found to decrease or avoid adverse gastrointestinal effects.

The actual preferred amounts of pharmaceutical composition in a specific case will vary according to the particular compositions formulated, the mode of application, the particular sites of application, and the subject being treated (e.g., age, gender, size, tolerance to drug, etc.).

Examples of typical daily amounts of NSAIDs to be administered in the methods of the present invention follows. The daily amounts can be administered in one dose, or in multiple doses, typically, two doses.

Naproxen from about 110 mg to about 1500 mg: Examples of other lower boundaries of this range include about 150 mg, about 220 mg, about 275 mg, about 320 mg and about 420 mg. Examples of other upper boundaries of this range include about 580 mg, about 680 mg, about 780 mg, about 880 mg and about 950 mg.

Ibuprofen from about 100 mg to about 3200 mg: Examples of other lower boundaries of this range include about 200 mg, about 400 mg, about 600 mg, about 700 mg, about 950 mg and about 1000 mg. Examples of other upper boundaries of this range include about 1200 mg, about 1500 mg, about 2000 mg, about 2500 mg and about 3000 mg.

Aspirin from about 250 mg to about 4000 mg: Examples of other lower boundaries of this range include about 325 mg, about 450 mg, about 550 mg, about 700 mg, about 1000 mg, about 1500 mg, and about 1800 mg. Examples of other upper boundaries of this range include about 2000 mg, about 2500 mg, about 3000 mg, about 3500 mg, and about 3800 mg.

Examples of typical daily amounts of the co-agent to be administered in the methods of the present invention follows. The daily amounts can be administered in one dose, or in multiple doses, typically, two doses.

Fexofenadine from about 25 mg to about 200 mg: Examples of other lower boundaries of this range include about 60 mg, about 70 mg, about 80 mg and about 90 mg. Examples of other upper boundaries of this range include about 100 mg, about 120 mg, about 150 mg and about 180 mg. Ketotifen from about 0.5 mg to about 3 mg: Examples of other lower boundaries of this range include about 1 mg, about 1.5 mg and about 1.8 mg. Examples of other upper boundaries of this range include about 2 mg, about 2.5 mg and about 2.8 mg. Desloratidine from about 2 mg to about 40 mg: Examples of other lower boundaries of this range include about 5 mg, about 6 mg and about 7 mg. Examples of other upper boundaries of this range include about 8 mg, about 9 mg and about 10 mg. Cetirizine from about 2 mg to about 10 mg: Examples of other lower boundaries of this range include about 5 mg, about 6 mg and about 7 mg. Examples of other upper boundaries of this range include about 8 mg, about 9 mg and about 10 mg.

In one embodiment of the invention, the pharmaceutical composition comprises about 800 mg ibuprofen and/or 220 mg naproxen and about 60 mg fexofenadine. For example, the pharmaceutical composition can be administered every twelve hours on a daily basis.

The pharmaceutical composition can be administered by methods known in the art. For example, the pharmaceutical composition can be administered systemically. For the purposes of this specification, "systemic administration" means administration to a human by a method that causes the compositions to be absorbed into the bloodstream.

In one embodiment, the pharmaceutical compositions are administered orally by any method known in the art. For example, the compositions can be administered in the form of tablets, including, e.g., orally-dissolvable tablets, chewable tablets; capsules; lozenges; pills (e.g., pastilles, dragees); troches; elixirs; suspensions; syrups; wafers; chewing gum; strips; films (e.g., orally-dissolving thin films); soluble powders; effervescent compositions; and the like.

The NSAID (and/or salt thereof) and the co-agent (and/or salt thereof) can be supplied in combination as one unit dose, or can be supplied individually, e.g., supplied in a package with a unit dose of NSAID and a unit dose of the co-agent.

Additionally, the pharmaceutical compositions can be administered enterally or parenterally, e.g., intravenously; intramuscularly; subcutaneously, as injectable solutions or suspensions; intraperitoneally; sublingually; or rectally (e.g., by suppositories). Administration can also be intranasally, in the form of, for example, an intranasal spray; or transdermally, in the form of, for example, a patch.

The pharmaceutical composition compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the pharmaceutically compositions can be employed, and the pH of the solutions can be suitably adjusted and buffered. For intravenous use, the total concentration of the solute(s) can be controlled in order to render the preparation isotonic.

A preferred embodiment of the invention is an orally dissolving tablet comprising an NSAID and a coagent with or without a taste masking ingredient, diluents, etc. Such tablet can be administered without water onto the tongue leading to immediate dissolution and is absorbed gastrointestinally or buccally. Orally dissolving tablets can be formulated by a number of techniques including compression and lyophilization, as would be known to a skilled artisan.

Another preferred embodiment of the invention is a lozenge or troche comprising an NSAID and a co-agent with or without a taste masking ingredient, diluents, etc. Such lozenge/troche can be administered without water, and can slowly dissolve in the mouth, or can be swallowed or chewed. Such lozenges/troches can be formulated by compression, as would be known to a skilled artisan.

The pharmaceutical compositions of the present invention can further comprise one or more pharmaceutically acceptable additional ingredient(s) such as alum, stabilizers, buffers, coloring agents, flavoring agents, and the like. In some embodiments, orally administered pharmaceutical compositions can contain breathe neutralizers, e.g., peppermint or menthol scents.

The pharmaceutical composition may be administered by controlled release. Controlled release administration is a method of drug delivery to achieve a certain level of the drug over a particular period of time. The level typically is measured by plasma concentration. Methods for controlled release of drugs are well known in the art.

The pharmaceutical compositions can be formulated for controlled release. For example, in one embodiment, the composition can be a capsule containing beadlets, wherein some of the beadlets dissolve instantaneously and some of the beadlets dissolve at delayed times due to different types of beadlet coatings.

In one embodiment, the pharmaceutical composition comprises an active ingredient, wherein the active ingredient consists of: a) NSAID, and/or salt thereof, and b) a co-agent selected from the group consisting of: fexofenadine, ketotifen, desloratadine, cetirizine, salts thereof and combinations thereof.

In one embodiment, the pharmaceutical composition consists of: a) NSAID, and/or salt thereof, b) a co-agent selected from the group consisting of: fexofenadine, ketotifen, desloratadine, cetirizine, salts thereof, and combinations thereof; and c) at least one carrier and/or excipient.

In one embodiment, the pharmaceutical composition consists essentially of the active ingredients of: a) NSAID and/or salt thereof, and b) a co-agent selected from the group consisting of: fexofenadine, ketotifen, desloratadine, cetirizine, salts thereof and combinations thereof. That is, any other ingredients that may materially affect the basic and novel characteristics of the active ingredients of the invention are specifically excluded from the composition. Any ingredient which can potentially cause an undesirable effect/side effect, including, for example, an allergic response, may materially affect the basic and novel characteristics of the active ingredients of the invention.

The following are some examples of components which may materially affect the basic and novel characteristics of the active ingredients of the pharmaceutical compositions and may be excluded from certain embodiments of the present invention: cyclooxygenase-2-selective inhibitors (i.e., COX-2-selective inhibitors) or prodrugs thereof; sedating antihistamines (e.g., phenyltoloxamine (e.g., phenyltoloxamine citrate), doxylamine (e.g., doxylamine succinate)); antiemetic antihistamines (e.g., dimenhydrinate (Dramamine®), clizines (e.g., cyclizine, meclizine), diphenhydramine (Benadryl®), promethazine (Pentazine®, Phenergan®, Promacot®), and hydroxyzine (Vistaril®)); decongestants; cough suppressants (e.g., guaifenesin, dextromethorphan); immunosuppressants (e.g., corticosteroids, methotrexate, azathioprine, cyclosporine, and leflunomide); disease-modifying anti-rheumatic drugs (DMARDs) (e.g., methotrexate), anti-TNFα agents (e.g., infliximab, adalimumab, and etanercept); sulfasalazine; 5-aminosalicylic acid; and $H_2$ antagonists.

The aforementioned ingredients may materially change the characteristics of the present pharmaceutical composition due to unwanted effects and/or potential allergic responses.

Examples of unwanted potential effects of COX-2-selective inhibitors, or prodrugs thereof, include an increased risk in the incidence of myocardial infarctions. COX-2-selective inhibitors are compounds which selectively inhibit cyclooxygenase-2 over cyclooxygenase-1, and also include pharmaceutically acceptable salts of such compounds, and prodrugs of such compounds. A COX-2 selective inhibitor is any inhibitor for which the ratio of COX-1 $IC_{50}$ to COX-2 $IC_{50}$ is greater than 1. Examples of COX-2 selective inhibitors are found in US2004/0029864, which patent publication is incorporated herein by reference in its entirety.

Examples of unwanted potential effects of sedating antihistamines, decongestants, cough suppressants and antiemetic antihistamines (e.g., diphenhydramine) include sleepiness, fatigue, dizziness, headache, dry mouth, difficulty urinating or an enlarged prostate and allergic reactions. Examples of unwanted potential effects of immunosuppressants (e.g., corticosteroids) include osteoporosis, fluid retention, edema, weight gain, high blood pressure, headache and muscle weakness. Examples of unwanted potential effects of DMARDs include stomach upset, nausea, diarrhea, infection, hair loss, liver damage and fatigue. Examples of unwanted potential effects of anti-TNFα agents include rashes, infections and tumor development. Examples of unwanted potential effects of sulfasalazine include blood disorder, liver damage, sore throat and fever. Examples of unwanted potential effects of 5-aminosalicylic acid include stomach upset, nausea/vomiting, constipation, headache, and joint/muscle pain. Examples of unwanted potential effects of $H_2$ antagonists include constipation, sexual dysfunction, drowsiness, dry mouth, and difficulty in urination.

The following are some additional examples of components which may materially affect the basic and novel characteristics of the active ingredients of the pharmaceutical compositions and may be excluded from certain embodiments of the present invention: ginsenoside, nicotinamide, nicotinamide adenine dinucleotide (NAD), agonists of cannabinoid receptors, N-benzyl pyrrole compounds, an anti-CGRP antibody/antibody fragment, 4-methylpyrazole, probiotics, a phosphodiesterase inhibitor (e.g., ibudilast), an opioid, acetaminophen, an adrenergic agent, an anticholinergic agent, zinc, pleconaril, a phosphodiesterase type 4 modulator, recombinant human uteroglobin, interleukin-9 and interleukin-8 antagonists, calcium glycerophosphate, flunixin meglumine (i.e., banamine), a 5-HT3 receptor antagonist, and $H_1$ antagonists other than fexofenadine, ketotifen, desloratadine, and cetirizine.

Examples of unwanted potential effects of ginsenoside include hormone-like effects, insomnia, increased heart rate, blood pressure variations, headache, diarrhea, itching, rash, dizziness, mood changes. Examples of unwanted potential effects of nicotinamide and NAD include upset stomach, nausea, vomiting, diarrhea, black/tarry stools, easy bruising/bleeding, edema, and jaundice. Examples of unwanted potential effects of agonists of cannabinoid receptors include difficulties with short-term memory, agitation, feeling tense, anxiety, dizziness or lightheadedness, confusion, and loss of coordination, episodes of psychosis and panic. Examples of unwanted potential effects of N-benzyl pyrrole compounds include allergic responses. Examples of unwanted potential effects of anti-CGRP antibody/antibody fragments include allergic reactions, fever and vomiting. Examples of unwanted potential effects of 4-methylpyrazole include elevation of serum transaminase values. Examples of unwanted potential effects of probiotics include gas, bloating, constipation and increased thirst. Examples of unwanted potential effects of phosphodiesterase inhibitors include GI distress, dizziness, headache, rash and elevated liver function tests. Examples of unwanted potential effects of opioids include GI distress, brain damage and dependence. Example of unwanted potential effect of acetaminophen includes liver damage. Examples of unwanted potential effects of an adrenergic agent include angina, hypertension or hypotension, tachycardia, arrhythmias, nervousness, headache, tremor, dry mouth, muscle cramps, palpitations, nausea, dizziness, fatigue, malaise, insomnia, hypokalemia, hyperglycemia, and metabolic acidosis. Examples of unwanted potential effects of anticholinergic agent include dry mouth, blurred vision, dry eyes, constipation, urinary retention, dizziness, cognitive problems, heart rhythm disturbance. Examples of unwanted potential effects of pleconaril include headache, diarrhea, and nausea. Examples of unwanted potential effects of phosphodiesterase type 4 modulators include nausea, vomiting, and related GI effects. Examples of unwanted potential effects of zinc include nausea, vomiting, diarrhea, metallic taste, kidney and stomach damage. Examples of unwanted potential effects of calcium glycerophosphate include taste problems and incomplete or infrequent bowel movements. Examples of unwanted potential effects of flunixin meglumine include ataxia, incoordination, hyperventilation, hysteria and muscle weakness. Examples of unwanted potential effects of 5-HT3 receptor antagonists include constipation, diarrhea, headache, dizziness and arrhythmias.

Thus, while there have been described what are presently believed to be the preferred embodiments of the present invention, other and further embodiments, modifications, and improvements will be known to those skilled in the art, and it is intended to include all such further embodiments, modifications, and improvements as come within the true scope of the claims as set forth below.

The invention claimed is:

1. A method of treating enteropathic arthritis in a human subject in need thereof, comprising:
   administering an effective amount of a pharmaceutical composition to the subject, wherein the pharmaceutical composition consists of:
   a) a non-steroidal anti-inflammatory drug (NSAID), and/or a salt thereof;
   b) a co-agent selected from the group consisting of: fexofenadine, ketotifen, desloratadine, cetirizine, salts thereof and combinations thereof; and
   c) optionally, a pharmaceutical carrier, a pharmaceutical excipient, a sweetening agent, a flavoring agent, a taste masking ingredient, a diluent, alum, a stabilizer, a buffer, a coloring agent, a breath neutralizer, an emulsifying agent, a suspending agent, and combinations thereof,
   wherein enteropathic arthritis is treated.

2. The method of claim 1, wherein the NSAID is selected from the group consisting of: aspirin, ibuprofen, naproxen, diclofenac, diflunisal, etodolac, indomethacin, ketoprofen, ketorolac, meloxicam, nabumetone, oxaprozin, piroxicam, salsalate, sulindac, and tolmetin.

3. The method of claim 1, wherein the NSAID is naproxen sodium and the co-agent is fexofenadine.

4. The method of claim 3, wherein the amount of naproxen sodium is about 220 mg to about 880 mg, and the amount of fexofenadine is about 60 mg to about 180 mg.

5. The method of claim 4, wherein the naproxen sodium and the fexofenadine are combined into a one unit dose.

6. The method of claim 5, wherein the naproxen sodium and the fexofenadine are in the form of an orally-dissolving tablet, lozenge or chewing gum.

7. The method of claim 2, wherein the amount of ibuprofen is about 200 mg to about 800 mg.

8. The method of claim 2, wherein the amount of aspirin is about 325 mg to about 1000 mg.

9. The method of claim 1, wherein the amount of ketotifen is about 0.5 mg to about 3 mg.

10. The method of claim 1, wherein the amount of desloratidine is about 5 mg to about 10 mg.

11. A method of treating enteropathic arthritis in a subject in need thereof, comprising:

administering to the subject an effective amount of a pharmaceutical composition, wherein the pharmaceutical composition consists of:
a) about 220 mg to about 880 mg of naproxen sodium, and about 60 mg to about 180 mg fexofenadine; and
b) optionally, a pharmaceutical carrier, a pharmaceutical excipient, a sweetening agent, a flavoring agent, a taste masking ingredient, a diluent, alum, a stabilizer, a buffer, a coloring agent, a breath neutralizer, an emulsifying agent, a suspending agent, and combinations thereof,
wherein the enteropathic arthritis is treated.

12. A pharmaceutical composition consisting of: a) an NSAID, and/or a salt thereof; b) a co-agent selected from the group consisting of:
fexofenadine, ketotifen, desloratadine, cetirizine salts thereof and combinations thereof; and c) optionally, a pharmaceutical carrier, a pharmaceutical excipient, a sweetening agent, a flavoring agent, a taste masking ingredient, a diluent, alum, a stabilizer, a buffer, a coloring agent, a breath neutralizer, an emulsifying agent, a suspending agent, and combinations thereof.

13. The pharmaceutical composition of claim 12, wherein the composition is in the form of an orally-dissolving tablet or lozenge.

14. The pharmaceutical composition of claim 12, wherein the NSAID is selected from the group consisting of: aspirin, ibuprofen, naproxen, diclofenac, diflunisal, etodolac, indomethacin, ketoprofen, ketorolac, meloxicam, nabumetone, oxaprozin, piroxicam, salsalate, sulindac, and tolmetin.

15. The pharmaceutical composition of claim 12, wherein the NSAID is naproxen sodium and the co-agent is fexofenadine.

16. The pharmaceutical composition of claim 15, wherein the amount of naproxen sodium is about 110 mg to about 900 mg, and the amount of fexofenadine is about 25 mg to about 200 mg.

* * * * *